United States Patent [19]

Swarup et al.

[11] Patent Number: 5,237,090
[45] Date of Patent: Aug. 17, 1993

[54] POLYMERIZABLE URETHANE ESTER VINYL REACTION PRODUCT

[75] Inventors: Shanti Swarup; Gregory J. McCollum, both of Gibsonia; Ronald M. Shewchuk, Allison Park; Jonathan T. Martz, Glenshaw, all of Pa.

[73] Assignee: PPG Industries, Inc., Pittsburgh, Pa.

[21] Appl. No.: 766,374

[22] Filed: Sep. 27, 1991

[51] Int. Cl.$^5$ .................................. C07C 271/10
[52] U.S. Cl. ........................ 560/32; 560/24; 560/33
[58] Field of Search ............ 560/24, 33, 32, 41, 560/160, 157

[56] References Cited

U.S. PATENT DOCUMENTS

| | | |
|---|---|---|
| 3,728,301 | 4/1973 | Spence et al. . |
| 4,042,413 | 8/1977 | Hauxwell et al. . |
| 4,129,455 | 12/1978 | Thompson et al. . |
| 4,157,266 | 6/1979 | Hauxwell et al. . |
| 4,163,749 | 8/1979 | Hauxwell et al. . |
| 4,166,066 | 8/1979 | Hauxwell et al. . |
| 4,604,439 | 8/1986 | Colvin .................................. 526/288 |

Primary Examiner—Christopher Henderson
Attorney, Agent, or Firm—Gary J. Connell; William J. Uhl

[57] ABSTRACT

A vinyl polymerizable reaction product useful in preparing pigment grind vehicles having improved grind time, viscosity properties and color properties is disclosed. The reaction product can be prepared by reaction of an ester with isopropenyl-α,α-dimethylbenzylisocyanate. The resulting product is a urethane ester which can be homopolymerized or copolymerized with other vinyl monomers. The invention is also directed toward the resulting polymeric grind vehicle and pigment pastes made therewith.

10 Claims, No Drawings

POLYMERIZABLE URETHANE ESTER VINYL REACTION PRODUCT

This invention relates to a novel vinyl polymerizable reaction product, and particularly to the use of such a reaction product in preparing a polymer useful as a pigment grind vehicle.

BACKGROUND OF THE INVENTION

In the production of pigmented paints, pigments are typically added to the paint as a component of a pigment paste which, in addition to pigment, also typically includes an organic resin. Pigments are commercially available in presscake or dry powder form and are made up of primary particles in the submicron size range. Primary pigment particles exist in various forms, such as aggregates, agglomerates, flocculates or combinations of these forms. To maximize the color properties of a pigment, such as strength, transparency, gloss, rheology and lightfastness, the pigment needs to be dispersed in a carrier medium in as finely divided a form as possible, preferably into primary pigment particles.

Dispersion of a pigment in a pigment paste is typically accomplished by subjecting a mixture of pigment and an organic resin, known as a grind vehicle, to a high shear and high stress process known as grinding or milling. The process of dispersion consists of (1) wetting the pigment surface with the resin, (2) deaggregating and deagglomerating pigment particles, and (3) stabilizing the dispersed pigment particles from flocculating upon standing or subsequent paint formulation.

Pigment grind vehicles have several important characteristics. Since many grinding processes are time intensive, the ability of a grind vehicle to disperse a pigment quickly to a given particle size is important.

A second important characteristic of a pigment grind vehicle is the ability to impart a low viscosity to a pigment paste at a given degree of grinding and to maintain low viscosity over time. When a pigment paste has good viscosity properties, higher resin solids paints can be prepared because the viscosity component of the paint due to the pigment paste will be less.

Another important characteristic of a pigment grind vehicle is the ability to achieve good color properties, such as those identified above, for a given pigment. Such properties principally relate to the degree of pigment dispersion which can be achieved by a grind vehicle.

While many commercial pigment grinding vehicles are available on the market, there exists a continuing need for pigment grinding vehicles which are improved in one or more of the above-described characteristics.

SUMMARY OF THE INVENTION

The present invention is directed toward a vinyl polymerizable reaction product of a mono-hydroxy functional ester and isopropenyl-α,α-dimethylbenzylisocyanate (TMI). In a preferred embodiment of the reaction product, the ester is a polyester derived from the reaction of an alcohol and a lactone. In particular, the lactone is ε-caprolactone and the alcohol is hexadecanol or butanol.

The polymerizable reaction product can also be characterized as having the following structure:

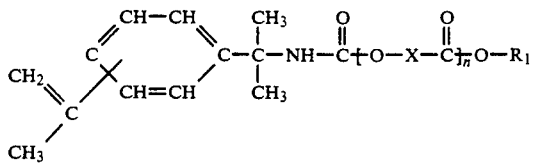

wherein n is >0, $R_1$ is alkyl or aralkyl and X is alkylene with greater than 2 carbon atoms. In a preferred embodiment, $R_1$ has from 1-20 carbon atoms and X is alkylene with 5 carbon atoms.

The present invention is also directed toward an ungelled vinyl polymer having pendant urethane ester groups. In a preferred embodiment of this polymer, the polymer also contains hydroxy and/or acid functional groups and the polymer is water reducible. A further embodiment of the invention includes a mixture of the ungelled vinyl polymer and a pigment.

DETAILED DESCRIPTION OF THE INVENTION

The present invention is directed toward a polymerizable reaction product of a mono-hydroxy functional ester and isopropenyl-α,α-dimethylbenzylisocyanate. The polymerizable reaction product is preferably used in preparing a polymer for use as a pigment grind vehicle. The pigment grind vehicle of the present invention has improved pigment grind vehicle properties over known grind vehicles.

The mono-hydroxy functional ester of the present invention can be a monoester or a polyester and is typically, but not necessarily, prepared from the reaction of a mono-alcohol and a lactone. The term mono-hydroxy functional ester refers to a monoester or polyester having an average of about one hydroxy group per molecule. The lactones useful in preparing the ester preferably have greater than 3 carbon atoms and more preferably from 6 to 11 carbon atoms. Accordingly, esters prepared from such lactones will have alkyl groups with greater than 2 and preferably from 5 to 10 carbon atoms attached to the carbonyl carbon of the ester. The lactone can also be selected from the group consisting of butyrolactone, ε- and γ-caprolactone, valerolactone, γ- and δ-decanolactone, δ-dodecanolactone, α-methyl-γ-butyrolactone and γ-nonanoiclactone. Most preferably, the lactone is ε-caprolactone. Also, hydroxy acids, such as hydroxy caproic acid can be used as functional equivalents to the use of lactones.

The mono-alcohol useful in preparing the ester of the present invention can be linear or branched and can be a primary, secondary or tertiary alcohol, although primary alcohols are preferred. Additionally, the alcohol can have from 1 to 20 carbon atoms. Preferably, the alcohol is selected from the group consisting of methanol, ethanol, butanol, hexadecanol, benzyl alcohol, decanol, and tridecanol. More preferably, the alcohol is butanol or hexadecanol.

The esters are typically prepared by reacting the mono-alcohol and lactone together. In this reaction, the hydroxyl group of the alcohol opens the lactone ring to generate a hydroxy functional ester. In the case of using a hydroxy acid instead of a lactone, the hydroxyl group of the alcohol reacts with the acid group to form an ester. The molar ratio of lactone to alcohol can range from 1:1 to 25:1 and preferably is about 7:1. At molar ratios greater than 1:1, some formation of polyesters will occur because after a lactone ring is opened by a hydroxyl group from an alcohol, the resulting hydroxy functional ester will react with another lactone to open the lactone ring to form a polyester with two ester units. The resulting reaction product from such a polyester will have repeating subunits and thus, will be considered a macromonomer. The components are mixed together with heat, for example, about 150° C., and catalyst, such as stannous octoate, until the reaction is complete as measured by the disappearance of lactone peaks from an IR spectrum or the disappearance of peaks of starting materials as determined by gas chromatography.

The resulting ester from the above reaction is then reacted with TMI. The isocyanate group on the TMI reacts with the hydroxy group from the hydroxy-functional ester to form a urethane linkage. The resulting reaction product has a vinyl group from the TMI which is available for homopolymerization or copolymerization with other vinyl monomers to form a vinyl polymer having pendant urethane ester groups. Such polymers are particularly useful as pigment grind vehicles. In preparation of the macromonomer, the mono-hydroxy ester and the TMI are reacted under mild heat, such as about 60° C., until the reaction is complete as determined by disappearance of isocyanate peaks from an IR spectrum. Other additives, such as catalysts, polymerization inhibitors, anticoloring agents and antioxidants can be used in the reaction in their customary manner as known by those skilled in the art.

A preferred embodiment of the polymerizable reaction product has the following structure:

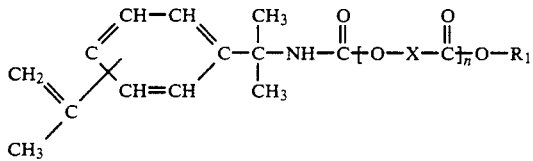

wherein n is >0, $R_1$ is alkyl or aralkyl and X is alkylene with greater than 2 carbon atoms. In a preferred embodiment, $R_1$ has from 1 to 20 carbon atoms and X is alkylene with 5 carbon atoms.

In alternative embodiments of the invention, the TMI can be either meta-isopropenyl-$\alpha,\alpha$-dimethylbenzylisocyanate (m-TMI) or para-isopropenyl-$\alpha,\alpha$-dimethylbenzylisocyanate (p-TMI). Instead of using TMI, other isocyanates having vinyl groups can also be used for reaction with the mono-hydroxy ester and subsequent polymerization. Any such isocyanate will form urethane esters and have vinyl groups available for polymerization. Other such isocyanates include isocyanatoethyl methacrylate (IEM) and ethylene isocyanate, as well as the 1:1 reaction product of hydroxy ethyl methacrylate with isophorone diisocyanate.

The present invention is also directed toward an ungelled vinyl polymer having pendant urethane ester groups, which is particularly useful as a grind vehicle. As noted above, one embodiment of such a polymer can be prepared by polymerizing the urethane ester reaction product of a mono-hydroxy ester and TMI with itself or with other vinyl monomers. Other vinyl monomers useful in forming such a copolymer include, but are not limited to, methyl methacrylate, butyl acrylate, styrene, acrylic acid, t-butylaminoethyl methacrylate, and hydroxyethylacrylate. The urethane ester reaction product of the present invention is typically present in a monomer mixture in amounts between about 5 weight percent and about 30 weight percent based on total weight of resin solids, more preferably between about 5 weight percent and about 20 weight percent and most preferably between about 8 weight percent and about 10 weight percent.

The vinyl monomers used for copolymerization with the reaction product of the present invention also preferably include at least one acid group-containing vinyl monomer, such as acrylic acid or methacrylic acid. In this manner, the subsequent polymer grind vehicle has acid functionality which, after neutralization with a base, makes the polymer water reducible. Typically, when the vinyl monomers include an acid group-containing monomer, the acid group-containing monomer is present in amounts between about 4 weight percent and about 10 weight percent based on total weight of resin solids, and more preferably between about 5 weight percent and about 8 weight percent, and most preferably between about 6.5 weight percent and about 7.5 weight percent.

The vinyl monomers used for copolymerization with the reaction product of the present invention also preferably include at least one hydroxyl group-containing monomer, such as hydroxy ethylacrylate. In this manner, the resulting polymer has hydroxyl functionality available for subsequent reaction, such as reactions that occur during cure of a paint incorporating the polymer. For example, many paints include aminoplast resins as crosslinkers which are reactive with hydroxyl groups. Typically, when the vinyl monomers include a hydroxyl group-containing monomer, the hydroxyl group-containing monomer is present in amounts between about 2 weight percent and about 20 weight percent based on total weight of resin solids and more preferably between about 5 weight percent and about 15 weight percent.

In polymerization of the vinyl monomers and the polymerizable reaction product of the present invention, the components are mixed together and added to solvent. The polymerizable components can then be polymerized at elevated temperatures, for example, between 80° C. and about 150° C., in the presence of a free radical initiator. The reaction is continued until completion as determined by measuring achievement of the total theoretical solids content of the monomer mixture or by other means known in the art. The reaction is typically conducted in an organic solvent, such as butanol. The weight average molecular weight of the polymer is preferably between about 10,000 and about 100,000, and more preferably between about 30,000 and about 60,000 as determined by gel permeation chromatography using a polystyrene standard.

In the case where an acid group-containing monomer is used in preparation of the polymer, the acid is subsequently neutralized with base. Water can then be added to the solution containing the polymer and, if desired, the organic solvent used for polymerization can be distilled off so that the polymer is dispersed in water alone.

A preferred embodiment of the present invention includes heating the polymer grind vehicle for a period of time prior to use in grinding pigment. More specifically, the polymer, either as a solvent borne or waterborne polymer, can be heated at between about 60° C. and about 100° C. and more preferably at about 80° C. for at least about 2 hours, more preferably at least about 5 hours and most preferably at least about 8 hours. The heating is preferably conducted during agitation of the dispersed polymer. The agitation can be, for example, mechanical stirring of the dispersion. It has been found, that significant advantages, such as, reduction in viscosity of the dispersed polymer, can be achieved in this manner.

After polymerization of the polymerizable reaction product of the present invention and other vinyl monomers, and regardless of whether the polymer is waterborne or solvent borne, the polymer can be used as a pigment grind vehicle. The present pigment grind vehicle is used in a conventional manner well known to those skilled in the art. In particular, pigment is added to the grind vehicle under high shear conditions until the pigment is well dispersed and the pigment is stabilized in the water or solvent by the grind vehicle. The resulting mixture is typically referred to as a pigment paste.

As mentioned above, grind vehicles prepared in accordance with the present invention have many improved properties, including grind time. The term grind time is known in the art and generally refers to the characteristic of a grind vehicle to disperse a pigment to a desired degree within a certain time. One common method of evaluating the degree of dispersion of a pigment is using a Hegman scale which measures dispersion by evaluating the size of dispersed pigment particles. For example, the grind time of two grind vehicles can be compared by grinding pigment with each vehicle at a constant pigment to binder ratio under the same conditions, such as those discussed in the examples, and comparing the time required to attain a given Hegman value.

Grind vehicles prepared in accordance with the present invention also have improved viscosity properties. Specifically, such grind vehicles impart a low viscosity to a pigment paste at a given degree of grinding. Moreover, pigment pastes and paints incorporating such grind vehicles maintain good viscosity over time and do not undergo irreversible changes in the degree of dispersion upon storage. Viscosity properties of grind vehicles can be evaluated, for example, by measuring the viscosity of a pigment paste after a standard time and temperature treatment, such as is discussed in the Examples.

Pigment grind vehicles of the present invention also provide improved color properties, such as strength, transparency, gloss, rheology and lightfastness. These properties can be evaluated by standard tests. For example, gloss can be tested by the procedure shown in the examples.

Pigment pastes prepared using the grind vehicle of the present invention can be conventionally used for preparing paint formulations. The resulting paints have the advantageous viscosity and color properties identified above with regard to pigment pastes.

Illustrating the invention are the following examples which, however, are not to be construed as limiting the invention to their details.

EXAMPLE 1

This Example illustrates the preparation of a monohydroxy polyester useful in preparing urethane polyester macromonomers.

A reaction vessel equipped with a stirrer, condenser, temperature probe and nitrogen sparge tube was charged with 1016.4 grams (g) (4.2 mol) of hexadecanol (Available from Aldrich Chemical Company), $\epsilon$-caprolactone (3183.6 g, 27.9 mol), 0.42 g butyl stannoic acid (Available from ATOCHEM North America) and 4.2 g triphenyl phosphite (Available from GE Plastics) and heated to 150° C. The contents of the reaction vessel were stirred until no evidence of $\epsilon$-caprolactone was evident by infrared spectral analysis. The reaction product when cooled became a waxy solid with an acid value of 1.93 mg KOH/g and a hydroxyl value of 57.5 mg KOH/g.

EXAMPLE 2

This Example illustrates the preparation of a urethane polyester macromonomer using the monohydroxy polyester of Example 1.

A reaction vessel equipped with a stirrer, condenser and a temperature probe was charged with 1500.0 g of the monohydroxy polyester of Example 1, 1.8 g dibutyltin dilaurate (Available from Air Products and Chemicals, Inc.), 450.0 g toluene and 1.8 g 2,6-di-t-butyl-p-cresol (Ionol) (from Shell Chemical Company) and heated to 60° C. Then, 301.6 g (1.5 mol) m-isopropenyl-$\alpha,\alpha$-dimethylbenzylisocyanate (m-TMI from American Cyanamid Company) was added over one hour. The contents of the reaction vessel were stirred until no evidence of isocyanate was present by infrared analysis.

EXAMPLE 3

This Example illustrates the use of an isocyanate functional monomer different from that in Example 2 to prepare a urethane polyester macromonomer using the monohydroxy polyester of Example 1.

A reaction vessel equipped with a stirrer, condenser and a temperature probe was charged with 500.0 g of the monohydroxy polyester of Example 1, 0.2 g Ionol, 0.4 g dibutyltin dilaurate and 150.0 g toluene and heated to 60° C. Then a solution of hydroxyethyl methacrylate isophorone diisocyanate adduct (mol ratio 1/1) in methyl isobutyl ketone (280.5 g, 0.5 equivalents) was added over two hours. The contents of the reaction vessel were stirred for five hours and 4.0 g n-butanol were added. The resulting reaction solution was stirred until no evidence of isocyanate was present by infrared analysis.

EXAMPLE 4

This Example illustrates the use of benzyl alcohol as the monoalcohol to prepare a monohydroxy polyester and a urethane polyester macromonomer.

A reaction vessel equipped with a stirrer, condenser, temperature probe and nitrogen sparge tube was charged with 108.0 g (1.0 mol) of benzyl alcohol (Available from AKZO Chemicals, Inc.), $\epsilon$-caprolactone (892.0 g, 7.8 mol), 0.2 g butyl stannoic acid and 0.02 g triphenyl phosphite, heated to 134° C., and the vessel contents stirred until no $\epsilon$-caprolactone was present as determined by infrared analysis. The reaction contents were cooled to 60° C. and 240.0 g toluene, 0.70 g Ionol and 1.2 g dibutyltin dilaurate were added all at once. Then, 201.0 g m-TMI was added over an hour and the reaction contents were stirred until no evidence of isocyanate was detectable by infrared analysis.

EXAMPLE 5

This Example illustrates the use of methanol as the monoalcohol to prepare a monohydroxy polyester and the subsequent urethane polyester macromonomer.

A reaction vessel equipped with a stirrer, condenser, temperature probe and nitrogen sparge tube was charged with 32.0 g (1.0 mol) methanol, 968.0 g (8.5 mol) ε-caprolactone, 0.05 g butyl stannoic acid and 0.025 g triphenyl phosphite and heated to 122° C. The reaction was monitored by infrared analysis until no ε-caprolactone was present. Then, the reaction contents were cooled to 60° C. and 0.3 g Ionol, 0.6 g dibutyltin dilaurate in 250.0 g toluene and 201.0 g m-TMI were added. The resultant solution was stirred at 60° C. until no evidence of isocyanate was present by infrared analysis.

EXAMPLE 6

This Example illustrates the use of 1-butanol as the monoalcohol to prepare a monohydroxy polyester and the subsequent urethane polyester macromonomer.

A reaction vessel equipped with a stirrer, condenser, temperature probe and nitrogen sparge tube was charged with 148.2 g (2.0 mol) 1-butanol, 1851.8 g (16.2 mol) ε-caprolactone, 0.2 g butyl stannoic acid and 0.02 g triphenyl phosphite and heated to 122° C. The reaction contents were stirred until no ε-caprolactone was present as determined by infrared analysis. After cooling to 60° C., a solution of 2.4 g dibutyltin dilaurate, 1.3 g Ionol and 600.0 g toluene was added followed by a one hour addition of 401.0 g m-TMI. The reaction vessel's contents were stirred at 60° C. until the isocyanate was no longer detectable by infrared analysis.

EXAMPLE 7

This Example illustrates the polymerization of the urethane polyester macromonomer of Example 6 with other vinyl monomers to prepare a useful solvent based pigment grind vehicle.

A reaction vessel equipped with a stirrer, thermometer, condenser and addition funnels was charged with 600.0 g butyl acetate and 121.0 g of the macromonomer from Example 6 and heated to reflux (about 122° C.). Two feeds, identified herein as "Feed A" and "Feed B", were gradually and simultaneously added to the vessel over a period of 3 hours while maintaining reflux conditions. Feed A consisted of 480.0 g methyl methacrylate, 360.2 g butyl acrylate, 60.0 g styrene, 60.0 g acrylic acid, 48.0 g hydroxy ethylacrylate and 9.6 g t-butylaminoethyl methacrylate. Feed B consisted of a mixture of 69.2 g t-amyl peroxyacetate (60 percent by weight in mineral spirits, LUPERSOL 555 from Pennwalt Corp.) and 200.0 g butyl acetate. After the addition of the two feeds A and B was complete, a mixture of 14.0 g LUPERSOL 555 and 25.0 g butyl acetate was added over 30 minutes followed by refluxing for an additional hour.

The resultant product has a total solids content measured for 1 hour at 110° C. of 53.0% by weight; has residual contents of methyl methacrylate, styrene and butyl acrylate, respectively of 0.07%, 0.02% and 0.01% by weight; has a Gardner viscosity of 0; has a weight average molecular weight of 12,318 and a number average molecular weight of 3873 as determined by gel permeation chromatography utilizing a polystyrene standard; and has an acid value of 22.3 mg KOH/g.

COMPARATIVE EXAMPLE 8

This Example illustrates the preparation of a polymer similar to that in Example 7, except that instead of using the urethane polyester macromonomer of Example 6, a monomer made by reacting butanol and m-TMI was used. The polymer of this Example was made according to the description in Example 7 except that the butanol/m-TMI monomer was prepared by reacting a 1:1 mole ratio of n-butanol with m-TMI at 60° C.

EXAMPLE 9

This Example illustrates the preparation of a polymer according to the description in Example 7, except that the macromonomer of Example 5 was used in place of urethane polyester macromonomer of Example 6.

EXAMPLE 10

This Example illustrates the preparation of a polymer according to the description in Example 7, except that the macromonomer of Example 2 was used in place of urethane polyester macromonomer of Example 6.

COMPARATIVE EXAMPLE 11

This Example illustrates the preparation of a polymer similar to that of Example 7, except that no urethane polyester macromonomer is used. The polymer of this Example is prepared in the same manner as the polymer of Example 7 except that the macromonomer of Example 6 was left out.

EXAMPLE 12

This Example illustrates the preparation of a urethane polyester macromonomer without any solvent using the following ingredients.

| Charge | |
|---|---|
| Butanol | 148.24 g |
| Caprolactone | 1851.8 g |
| Butyl Stannoic Acid | 0.2 g |
| Triphenyl Phosphite | 0.02 g |
| Feed A | |
| Dibutyltin Dilaurate | 2.4 g |
| Di-t-Butyl-p-Cresol | 1.3 g |
| Feed B | |
| m-Isopropenyl-Dimethyl-Benzylisocyanate | 402.0 g |

The charge was added into a 5 liter flask equipped with a thermometer, stirrer, and external heating. The flask contents were heated to about 140° C. and maintained at this temperature for about 6 hours until the caprolactone is all reacted as measured by I.R. spectroscopy.

The contents of the flask were then cooled to 60° C. Feed A was then added, followed by addition of Feed B over one hour. The contents of the flask were maintained at this temperature until isocyanate peaks disappeared in I.R. spectrum. The product was cooled and collected.

This product has $M_n$ 1509, $M_w$ 2410, $M_z$ 3474 and polydispersity 1.59 as measured by gel permeation chromatography analysis. Equivalent weight was 1459 as measured by iodine titration. The product was 100% solids.

EXAMPLE 13

This Examples illustrates the preparation of a water based pigment grind vehicle by polymerization of the urethane polyester macromonomer of Example 12 with other vinyl monomers using the following ingredients.

| Charge | |
|---|---|

| -continued | |
|---|---|
| Butanol | 200.0 g |
| Macromonomer (Example 12) | 80.2 g |
| Feed A | |
| Styrene | 80.6 g |
| Butyl Acrylate | 260.5 g |
| Methyl Methacrylate | 320.1 g |
| Hydroxy Ethyl Acrylate | 80.6 g |
| Acrylic Acid | 60.0 g |
| Feed B | |
| Tertiary Butyl Peracetate | 28.7 g |
| Butanol | 92.7 g |
| Feed C | 55.6 g |
| Dimethyl Ethanol Amine | |
| Feed D | 2191.6 g |
| Deionized Water | |

The charge was added into a 5 liter flask equipped with a thermometer, stirrer, and external heating. This charge was then heated to reflux followed by addition of Feeds A and B over three hours. Upon completion of Feeds A and B, the contents of the flask were cooled down to about 100° C. Feed C was then added over 10 minutes, followed by Feed D.

The total solids content of the product was 25.4%. Gel permeation chromatography analysis showed $M_n$ 8882, $M_w$ 47489, $M_z$ 98412 and a polydispersity of 5.3.

EXAMPLE 14

This Example illustrates the preparation of a water based pigment grind vehicle by polymerization of the urethane polyester macromonomer of Example 12 with other vinyl monomers using the same ingredients and procedures of Example 13, except the butanol in the charge was replaced by butyl carbitol.

COMPARATIVE EXAMPLE 15

This Example illustrates the preparation of a water based pigment grind vehicle by polymerization of vinyl monomers. The polymer of this Example is prepared using the same ingredients and procedures of Example 13, except no urethane polyester macromonomer was used.

EXAMPLE 16

This Example illustrates the preparation of a water based pigment grind vehicle by polymerization of the urethane polyester macromonomer of Example 12 with other vinyl monomers using the same ingredients and procedures of Example 13, except the amount of macromonomer was doubled in the charge.

EXAMPLE 17

This Example compares the grind times and viscosity characteristics of the solvent based grind vehicles of Examples 7-11.

A solvent mixture of butyl acetate was used. 361.1 g of the resins in each of Examples 7-11 was added to a separate vessel with 66.1 ml. of solvent. The resins were then agitated with a Cowles blade for 10 minutes. Carbon black pigment was added at a pigment to binder ratio of 0.28. This mixture was agitated with a Cowles blade for 15 minutes. The resulting paste was passed through an Eiger Mill (Model #250) (Eiger Machine, Inc. of Chicago, Ill.) operating at 4000 rpm until a Hegman reading of greater than 7.0 is attained. The time required to attain a Hegman reading of 7.0 is considered to be the grind time.

The viscosity characteristics of the resins were evaluated by further grinding each of the above-described pastes in an Eiger Mill at 4000 rpm for 90 minutes and storing the paste at room temperature overnight. The viscosity is then measured using a Brookfield viscometer, model RVT using spindle needle #4 at 6 rpm.

The results of grind time and viscosity evaluations for the resins in Examples 7-11 are shown below in Table 1.

TABLE 1

| Grind Time/Viscosity Evaluation for Examples 7-11 | | |
|---|---|---|
| Example | Grind Time (minutes) | Viscosity[a] (cps) |
| 7 | 20 | 3,500 |
| 8 (comparative) | 40 | 7,560 |
| 9 | 20 | 4,625 |
| 10 | 35 | 4,050 |
| 11 (comparative) | 60 | 8,825 |

[a]Viscosity measured using a Brookfield viscometer, model RVT, with a spindle needle #4 at 6 rpm after paste was further ground and stored as described above.

As can be seen from Table 1, the three resins of the present invention provided better grind times and improved viscosity as compared with the comparative Examples.

EXAMPLE 18

This Example compares the grind time, viscosity characteristics and color development of the water based grind vehicles of Examples 13-16.

A solvent mixture of 1 part of Dowanol PM, 1 part of Propasol P and 2 parts of deionized water was used. 457.3 g of the grinding resin in each of Examples 13-16 was added to a separate vessel with 173.2 ml. of solvent. The pH of the medium was adjusted to 8.15 by adding dimethylethanol amine. This mixture was agitated with a Cowles blade for 10 minutes. Carbon black pigment was then added at a pigment to binder ratio of 0.28. The mixture was agitated with a Cowles blade for 15 minutes. The resulting paste was then passed through Eiger Mill (Model #250) operating at 4000 rpm until a Hegman reading of 7.0 is attained.

The grind time and viscosity are determined as discussed above in Example 17.

TABLE 2

| Grind Time/Viscosity Evaluation for Examples 13-16 | | |
|---|---|---|
| Examples | Grind Time (minutes) | Viscosity (cps) |
| 13 | 50 | 580 |
| 14 | 60 | 600 |
| 15 (comparative) | 90 | —[a] |
| 16 | 45 | 611 |

[a]The resin of Comparative Example 15 was too viscous to obtain a viscosity measurement.

As can be seen in Table 2, all resins prepared in accordance with this invention had a significantly faster grind time than Comparative Example 15 and the viscosity of Example 15 could not be measured.

EXAMPLE 19

This Example compares the color properties in terms of gloss of the resins in Examples 13 and 15.

Pigment pastes were prepared using the resins of Examples 13 and 15 in the manner described in Example 18. The pastes were drawn down to a thickness of 1.7 mils on a 5 mil thick polypropylene film, which was stored at room temperature for 10 minutes. This film was then baked for 20 minutes at 250° F. The baked films were then examined subjectively for gloss on a scale of 0-5 (5 being the best). Three different pigments were used: carbon black, pthalo blue and red iron oxide. The results are shown in Table 3.

TABLE 3

| | Gloss of Examples 13 and 15 | | |
|---|---|---|---|
| | Color Development | | |
| Example | Carbon Black | Pthalo Blue | Red Iron Oxide |
| 13 | 5 | 5 | 5 |
| 15 (comparative) | 3 | 3 | 2 |

As can be seen from Table 3, the gloss of Example 13 was significantly better than that of Comparative Example 15.

EXAMPLE 20

This Example illustrates an embodiment of the invention in which a polymer grind vehicle of the invention is heated at elevated temperature. The polymer dispersion of Example 13 was evaluated for total solids, molecular weight, viscosity and particle size. The polymer dispersion of Example 13 was then held at 80° C. for eight hours under agitation and subsequently reevaluated after cooling for total solids, molecular weight, viscosity and particle size. The results are shown below in Table 4.

TABLE 4

| Comparison of Example 13 Properties Before and After Extended Heating | | | |
|---|---|---|---|
| | Total Solids (%) | Molecular Weight (Mw) | Viscosity (cps) | Particle Size (nm) |
| Before heating | 25.4 | 47489 | 1130 | 110 |
| After heating | 25.4 | 47489 | 760 | 143 |

As can be seen from Table 4, a significant reduction in viscosity was attained by the treatment in this Example.

What is claimed is:

1. A vinyl polymerizable reaction product of:
   (1) a mono-hydroxy functional ester which is derived from the reaction product of an alcohol and a lactone or a hydroxy acid and
   (2) isopropenyl-α,α-dimethylbenzylisocyanate.

2. A reaction product as claimed in claim 1, wherein said ester has an alkylene group bonded to the carbonyl carbon of the ester with 2 or more carbon atoms.

3. A reaction product as claimed in claim 2, wherein said alkylene group contains from 5 to 10 carbon atoms.

4. A reaction product as claimed in claim 1, wherein said ester is derived from the reaction of an alcohol and a lactone.

5. A reaction product as claimed in claim 4, wherein the ring structure of said lactone has from four to eleven carbon atoms.

6. A reaction product as claimed in claim 5, wherein said lactone is ε-caprolactone.

7. A reaction product as claimed in claim 4, wherein said alcohol is selected from the group consisting of alcohols having from 1-20 carbon atoms.

8. A reaction product as claimed in claim 7, wherein said alcohol is hexadecanol or butanol.

9. The composition of claim 1, wherein said isopropenyl-α,α-dimethylbenzylisocyanate is m-isopropenyl-α,α-dimethylbenzylisocyanate.

10. A polymerizable reaction product having the following structure:

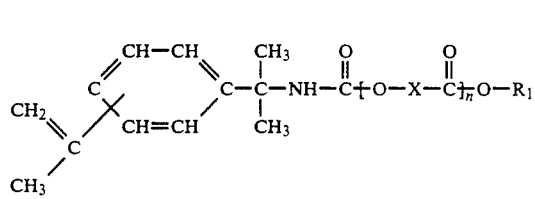

wherein n is $>0$, $R_1$ is alkyl or aralkyl and X is alkylene with greater than 2 carbon atoms.

* * * * *